United States Patent [19]

Hauser

[11] Patent Number: 5,133,353
[45] Date of Patent: Jul. 28, 1992

[54] IMPLANTABLE INTRAVENOUS CARDIAC STIMULATION SYSTEM WITH PULSE GENERATOR HOUSING SERVING AS OPTIONAL ADDITIONAL ELECTRODE

[75] Inventor: Robert G. Hauser, Long Lake, Minn.

[73] Assignee: Cardiac Pacemakers, Inc., St. Paul, Minn.

[21] Appl. No.: 514,251

[22] Filed: Apr. 25, 1990

[51] Int. Cl.⁵ .............................................. A61N 1/39
[52] U.S. Cl. .............................. 128/419 D; 128/419 P
[58] Field of Search ........ 128/419 D, 419 P, 419 PG, 128/419 PS, 784

[56] References Cited

U.S. PATENT DOCUMENTS

| | | | |
|---|---|---|---|
| 3,602,229 | 8/1971 | Jaros et al. | 128/421 |
| 3,614,954 | 10/1971 | Mirowski et al. | 128/419 D |
| 3,835,864 | 9/1974 | Rasor et al. | 128/419 P |
| 3,866,616 | 2/1975 | Purdy et al. | 128/419 PS |
| 4,157,720 | 6/1979 | Greatbatch | 128/419 P |
| 4,289,134 | 9/1981 | Bernstein | 128/419 PG |
| 4,291,707 | 9/1981 | Heilman et al. | 128/419 D |
| 4,375,817 | 3/1983 | Engle et al. | 128/419 D |
| 4,558,702 | 12/1985 | Barreras et al. | 128/419 PG |
| 4,790,318 | 12/1988 | Elmqvist | 128/419 PG |
| 4,825,871 | 5/1989 | Cansell | 128/419 D |
| 5,012,806 | 5/1991 | De Bellis | 128/419 P |

*Primary Examiner*—William E. Kamm
*Attorney, Agent, or Firm*—Fleit, Jacobson, Cohn, Price, Holman & Stern

[57] ABSTRACT

A pulse generator housing for enclosing and containing pulse generator defibrillation circuitry. At least one surface is electrically conductive and connected to the pulse generator circuitry for delivering defibrillating energy to the heart. The pulse generator housing is implanted in the pectoral region proximate the heart with the conductive surface facing the heart. Other implantable electrodes are discharged against the pulse generator housing electrode. Specifically, particular ones of the implantable electrodes are selected for discharge against the pulse generator housing according to detected heart conditions.

11 Claims, 3 Drawing Sheets

IMPLANTABLE INTRAVENOUS CARDIAC STIMULATION SYSTEM WITH PULSE GENERATOR HOUSING SERVING AS OPTIONAL ADDITIONAL ELECTRODE

BACKGROUND OF THE INVENTION

This invention relates to an implantable cardiac stimulation lead and electrode system for applying electrical energy to an abnormally functioning heart.

Electrodes implanted in the body for electrical stimulation of muscle or body organs are well known. More specifically, electrodes implanted on or about the heart have been used to reverse certain abnormal and life-threatening arrhythmias. Electrical energy is applied to the heart via the electrodes to return the heart to normal sinus rhythm.

Common abnormal cardiac arrhythmias include bradycardia (slower than normal heartbeat rhythm), ventricular tachycardia (faster than normal heartbeat rhythm), and ventricular fibrillation (sporadic and uncoordinated beating of the heart). The latter two arrhythmias generally are fatal if left untreated.

To control the heartbeat rhythm and prevent fatalities from ventricular tachycardia and fibrillation, several devices have been designed having the ability to stimulate the heart according to a sensed cardiac signal such as a sensed ECG signal. See for example U.S. Pat. No. 4,603,705 to Speicher et al. The Speicher et al. patent discloses a multiple electrode unitary intravascular cardiac catheter having a distal electrode for sensing and pacing, an intermediate electrode for sensing, pacing and cardioverting, and a proximal electrode for sensing and cardioverting. This multiple electrode catheter maintains the ability for heart rate sensing and low threshold pacing immediately following cardioversion.

The need therefore exists for implantable cardiac stimulation lead system capable of performing standard pacing, such as anti-bradycardia pacing, anti-tachycardia pacing, low-energy cardioversion, and high-energy defibrillation.

SUMMARY OF THE INVENTION

It is a primary object of this invention to provide an implantable cardiac stimulation lead system having pacemaking, cardioversion and higher energy defibrillation capabilities.

It is an additional object of this invention to provide an implantable cardiac stimulation lead system having pacemaking, cardioversion and defibrillation capabilities via a selectable electrode configuration.

It is yet a further object of this invention to provide an implantable cardiac stimulation lead system utilizing a relatively small number of implantable parts.

Briefly, the implantable cardiac stimulation lead system of the present invention comprises a transvenous myocardial, or pericardial lead having a plurality of electrodes. Typically, the lead electrodes are capable of sensing and performing standard anti-bradycardia pacing, anti-tachycardia pacing, cardioversion and defibrillation. The transvenous lead is connected to a pulse generator having full-function pacing capabilities as well as cardioversion and defibrillation capabilities. The housing of the pulse generator is conductive and is connected to the pulse generator circuitry so that it may selectively serve as a discharge electrode. The outer surface of the pulse generator could be of a special configuration to facilitate its discharge capabilities. Typically, the pulse generator is implanted in the pectoral or abdominal region of the body proximate the heart. A programmable switch or other type of circuitry is provided to select the electrode configuration which may include or exclude the pulse generator housing electrode. As a result, different electrode configurations ca be obtained for specific types of cardiac stimulations.

The above objects and advantages of the present invention can be further understood when reference is made to the following description, taken in conjunction with the accompanying drawings.

DETAILED DESCRIPTION OF THE DRAWINGS

Figure 1:
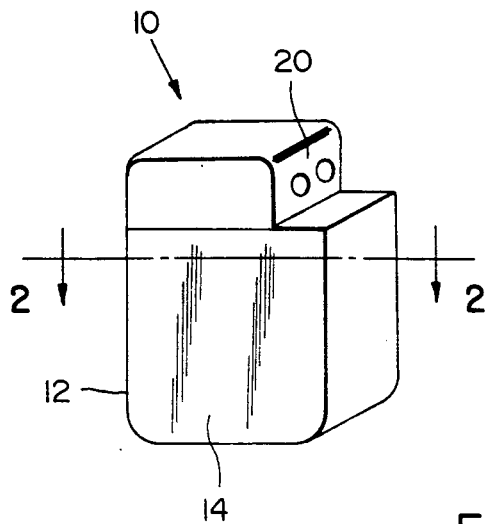
FIG. 1 is a perspective view illustrating the pulse generator housing serving as a cardiac electrode in accordance with a first embodiment of the present invention.
Figure 2:
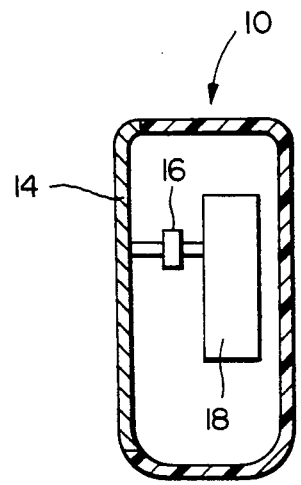
FIG. 2 is a cross-sectional view taken through line 2—2 of FIG. 1.

Referring to FIGS. 1 and 2, the pulse generator housing of the present invention is generally shown at 10. Typically, housing 10 is of a rectangular box shape having four side walls, a top wall, and a bottom wall. In one embodiment, at least one of the side walls is highly conductive. To this end, housing 10 includes side wall 12 having an outer discharge surface 14 formed of highly electrically conductive material. The conductive surface 14 is connected to the pulse generator circuitry 18 via a programmable switch 16. The pulse generator circuitry 18 is also electrically connected to electrode lead plug receptacle 20.

As previously mentioned, the number of side walls of housing 10 having conductive discharged surfaces may vary. However, it is envisioned that as many as four side walls may be made electrically conductive.

Figure 3:
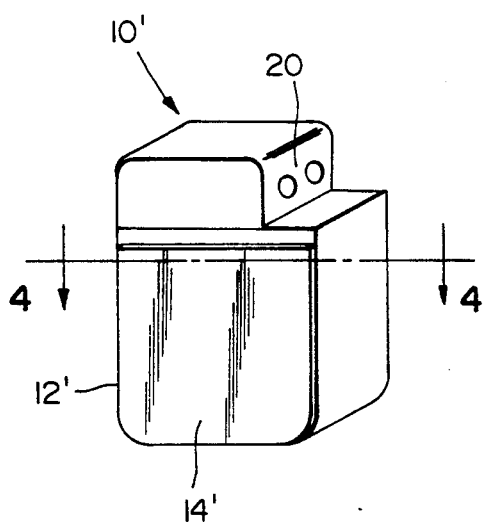
FIG. 3 is a perspective view illustrating the pulse generator housing having conductive mesh on a face thereof for serving as a cardiac electrode in accordance with the second embodiment of the present invention.
Figure 4:
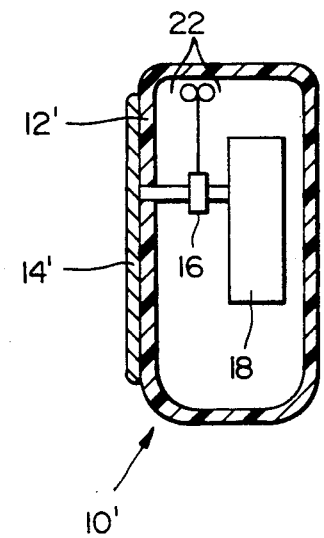
FIG. 4 is a cross-sectional view taken through line 4—4 of FIG. 3.
Figure 6:
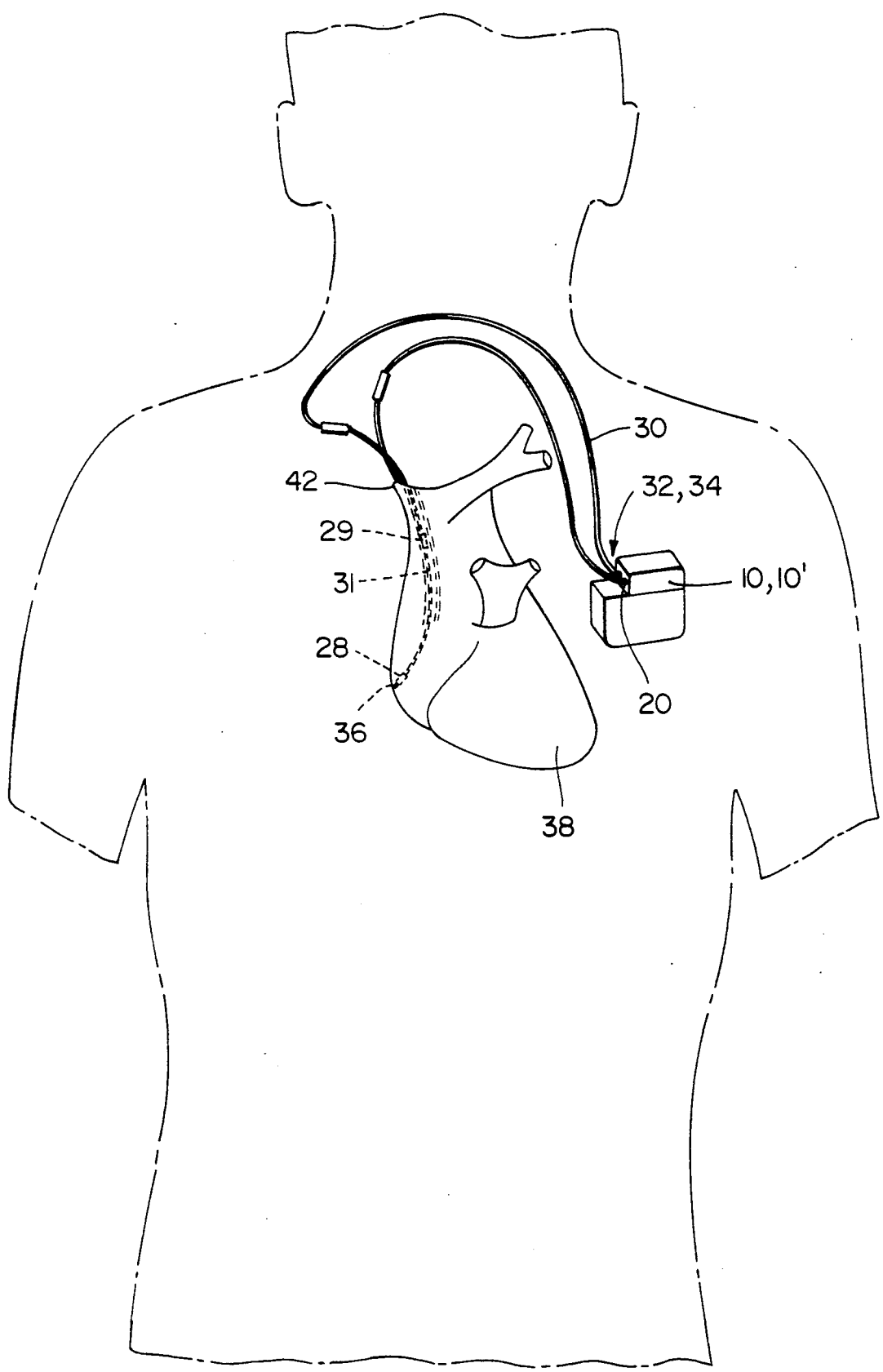
FIG. 6 is a diagram illustrating the placement of the pulse generator housing adjacent the heart and connected to the implanted transvenous electrode and lead.

Referring now to FIGS. 3 and 4, a pulse generator housing of a second embodiment is illustrated at 10'. Housing 10' is similar to housing 10 of FIGS. 1 and 2 except the side wall 12' includes a conductive mesh surface 14'. It is to be understood that, hereinafter, the term "mesh" includes that as illustrated as well as any other high surface area conductive materials. As shown in FIG. 6, conductive mesh surface 14' is electrically connected via switch 16 to pulse generator circuitry 18 contained within housing 10'. In addition a separate conductive patch (not shown) could be added and connected to the bottom of the pulse generator housing to increase the conductive surface area. This patch could attach by a snap or other similar means to the housing.

Figure 7:
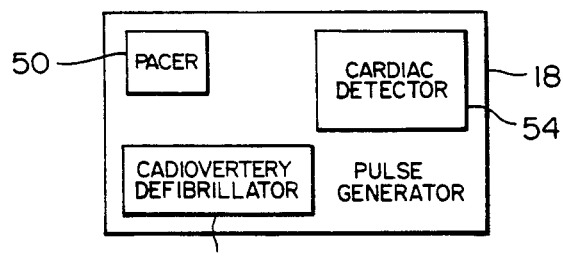
FIG. 7 is a block diagram illustrating the pulse generator.

Referring to FIG. 7, pulse generator circuitry 18 has full-function pacing capabilities (pacer 50) including pacing for bradycardia and tachycardia both to inhibit an intrinsic beat or to adapt the rate to a higher or lower rate. In addition, circuitry 18 has cardioversion and defibrillation capabilities (cardioverter/defibrillator 52) and includes cardiac detection circuitry 54 capable of distinguishing when the heart is in normal sinus rhythm, should be paced, or requires higher energy cardioversion, or even higher energy defibrillation. The switch 16 is selectively activated to include or exclude the conductive surface of side wall 12 from the discharge sequence.

Figure 5:
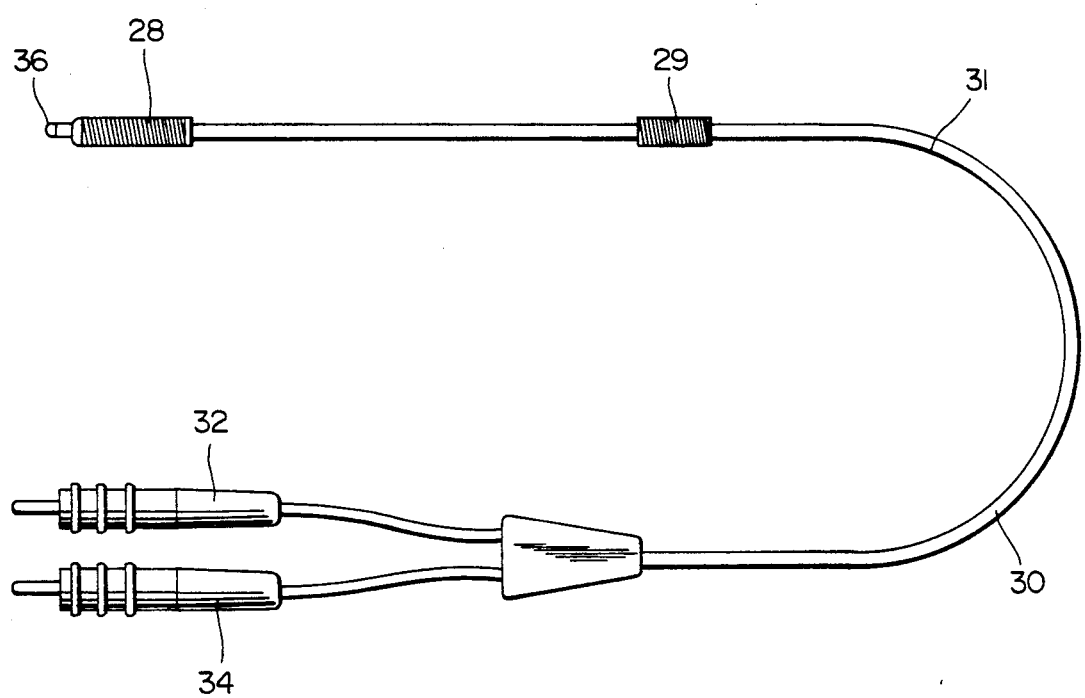
FIG. 5 is a side view of a transvenous electrode and lead used in conjunction with the pulse generator illustrated in FIG. 1 or FIG. 3.

Pulse generator housing 10 or 10' is typically used in conjunction with other cardiac electrodes implanted on or about a human heart. One such lead is illustrated in FIG. 5. Lead 30 is provided having a catheter portion 31 supporting electrode 28 on the distal end as well as electrode 29 on a proximate end of catheter portion 31. Lead 30 includes plug connectors 32 and 34 at its proximal end. In addition, a sensing tip electrode 36 may be provided at the distal tip of catheter portion 31 for sensing cardiac activity. Electrodes 28 and 29 could also have sensing capabilities.

Referring to FIG. 6, in operation, lead 30 is implanted transvenously in the human heart 38 with electrode 28 in the right ventricle 40 and electrode 29 proximate the right atrium or the superior vena cava 42. Alternatively, a single catheter electrode may be used for placing the electrode in the right ventricle. Pulse generator housing 10 or 10' is implanted in the pectoral region proximate but not in contact with the heart, just under the skin, with its conductive side wall(s) facing the heart. Alternatively, the housing 10 or 10' could be implanted in the abdominal region. Plug connectors 32 and 34 are inserted into receptacle assembly 20.

When an arrhythmia is sensed where it is appropriate for an electrical shock to be delivered to the heart 38, the programmable switch 18 determines which electrodes are energized under control of circuitry 18. If the heart activity is slower or faster (bradycardia or tachycardia) than normal, the switch 16 is triggered so that the pulse generator circuitry 18 selects only electrode 28. On the other hand, if the sensed activity is indicative of rapid ventricular tachycardia or fibrillation requiring higher energy stimulation, the switch 16 is triggered so that the pulse generator circuitry 18 selects both distal and proximal electrodes 28 and 29, respectively, as well as the electrode discharge surface 14 to discharge energy from the conductive wall(s) of housing 10 or 10' for delivering electrical energy to the heart 38 for generating a defibrillating electric field across the heart.

Alternatively, prior to applying a high energy defibrillating shock to the heart, a lower energy cardioverting shock can be applied between electrodes 28 and 29 against the conductive wall(s) of the pulse generator housing 10 or 10'. Thereafter, if the heart does not revert back to normal sinus rhythm, the higher energy defibrillation pulse is applied across the same electrodes.

In yet another alternate form, the programmable switch 18 may be programmed to select one of the electrodes 28 and 29, and the electrode discharge surface 14 of the pulse generator housing 10 or 10'. In this way, the electrode discharge surface 14 of the pulse generator housing 10 or 10' will be discharged against only one of the electrodes 28 and 29. Further, the choice between the electrodes 28 and 29 may be based on certain cardiac conditions.

It is considered that the above description is intended by way of example only, and is not intended to limit the present invention in any way except as set forth in the following claims.

I claim:

1. An implantable heart treatment system having anti-arrhythmia pacemaking, cardioversion, and defibrillation capabilities for maintaining proper function of the heart, said system comprising:

an implantable pulse generator means for producing an anti-arrhythmia waveform including a defibrillation/cardioversion waveform;

a pulse generator housing enclosing and containing said pulse generator means, said pulse generator housing including a conductive surface comprised of electrically conductive mesh which is electrically connected to said pulse generator means for delivering electrical energy to the heart, said housing for implantation proximate the heart with said conductive surface facing the heart;

a first electrode for implantation in the region of the heart and being electrically connected to said pulse generator;

a second electrode for implantation in the region of the heart and being electrically connected to said pulse generator;

switching means connected to said pulse generator means for directing a cardioversion/defibrillation waveform on the one hand, to said first and second electrodes upon a first condition of said heart, and on the other hand directing a cardioversion/defibrillation waveform to said first and second electrodes to said conductive surface of said pulse generator housing upon a second condition of the heart.

2. The implantable heart treatment system of claim 1, and further including detection means connected to said switching means for sensing at least said first and second conditions of the heart and for controlling the switching means.

3. The implantable heart treatment system of claim 2, wherein said detection means includes means for detecting ventricular fibrillation as said second condition.

4. An implantable heart treatment system having anti-arrhythmia pacemaking, cardioversion, and defibrillation capabilities for maintaining proper function of the heart, said system comprising:

an implantable pulse generator for producing an anti-arrhythmia waveform including a defibrillation/cardioversion waveform;

a pulse generator housing enclosing and containing said pulse generator, said pulse generator housing comprising a plurality of walls, at least one of said walls having an electrically conductive outer surface comprised of electrically conductive mesh which is electrically connected to said pulse generator, said pulse generator housing for implantation proximate the heart with said electrically conductive surface of said pulse generator housing facing the heart for delivering electrical energy to the heart;

a first electrode for implantation in the region of the heart and electrically connected to said pulse generator;

a second electrode for implantation in the region of the heart and electrically connected to said pulse generator;

switching means connected to said pulse generator for directing, on the one hand a cardioversion/defibrillation waveform to said first and second electrodes upon a first condition of said heart, and on the other hand directing a cardioversion/defibrillation waveform to said first and second electrodes and to said electrically conductive surface of said pulse generator housing upon a second condition of the heart.

5. The implantable heart treatment system of claim 4, and further including detection means connected to said switching means for sensing at least said first and second conditions of the heart and controlling the switching means.

6. The implantable heart treatment system of claim 5, wherein said detection means includes means for detecting ventricular fibrillation as said second condition.

7. An implantable heart treatment system having anti-arrhythmia pacemaking, cardioversion, and defibrillation capabilities for maintaining proper function of the heart, said system comprising:

an implantable pulse generator for producing an anti-arrhythmia waveform including a defibrillation/cardioversion waveform;

a pulse generator housing enclosing and containing said pulse generator, said pulse generator housing comprising a plurality of walls, at least one of said walls having an electrically conductive outer surface comprised of electrically conductive mesh which is electrically connected to said pulse generator, said pulse generator housing for implantation proximate the heart with said conductive surface facing the heart for delivering electrical energy to the heart;

a transvenous lead having a first electrode at a distal end thereof and a second electrode at an intermediate portion thereof, said lead for implantation in the heart so that said first electrode is positioned in the right ventricle and said second electrode is positioned in the vena cava region of the heart, said lead electrically connecting said first and second electrode to said pulse generator;

switching means connected to said pulse generator for directing on the one hand, a cardioversion/defibrillation waveform to said first and second electrodes upon a first condition of the heart, and on the other hand directing a cardioversion/defibrillation waveform to said first and second electrodes and to said conductive outer surface of said pulse generator housing upon a second condition of the heart.

8. The implantable heart treatment system of claim 7, and further including detection means connected to said switching means for sensing at least said first and second conditions of the heart and for controlling the switching means.

9. The implantable heart treatment system of claim 8, wherein said detection means includes means for detecting ventricular fibrillation as said second condition.

10. An implantable heart treatment system having anti-arrhythmia pacemaking, cardioversion, and defibrillation capabilities for maintaining proper function of the heart, said system comprising:

an implantable pulse generator means for producing an anti-arrhythmia waveform;

a pulse generator housing enclosing and containing said pulse generator means, said pulse generator housing including a conductive surface comprised of electrically conductive mesh which is electrically connected to said pulse generator means for delivering electrical energy to the heart, said housing for implantation proximate the heart;

an implanted electrode for implantation about the heart and being electrically connected to said pulse generator for delivering electrical energy to the heart against said conductive surface of said pulse generator housing.

11. An implantable heart treatment system having anti-arrhythmia pacemaking, cardioversion, and defibrillation capabilities for maintaining proper function of the heart, said system comprising:

an implantable pulse generator means for producing a low energy cardioversion waveform and a higher energy defibrillation waveform;

a pulse generator housing enclosing and containing said pulse generator means, said pulse generator housing including a conductive surface comprised of electrically conductive mesh which is electrically connected to said pulse generator means for delivering electrical energy to the heart, said housing for implantation proximate the heart with said conductive surface facing the heart;

a first electrode for implantation in the region of the heart and being electrically connected to said pulse generator;

a second electrode for implantation in the region of the heart and being electrically connected to said pulse generator;

switching means connected to said pulse generator means for directing said low energy cardioversion waveform on the one hand, to at least one of said first and second electrodes and to said conductive surface of said pulse generator housing upon a first condition of said heart, and on the other hand directing said higher energy defibrillation waveform to said first and second electrodes and to said conductive surface of said pulse generator housing upon a second condition of the heart.

* * * * *